(12) United States Patent
Cao et al.

(10) Patent No.: US 10,502,692 B2
(45) Date of Patent: Dec. 10, 2019

(54) AUTOMATED METROLOGY SYSTEM SELECTION

(71) Applicant: KLA-Tencor Corporation, Milpitas, CA (US)

(72) Inventors: Meng Cao, Union City, CA (US); Lie-Quan Lee, Fremont, CA (US); Qiang Zhao, Milpitas, CA (US); Heyin Li, Shanghai (CN); Mengmeng Ye, Shanghai (CN)

(73) Assignee: KLA-Tencor Corporation, Milpitas, CA (US)

( * ) Notice: Subject to any disclaimer, the term of this patent is extended or adjusted under 35 U.S.C. 154(b) by 211 days.

(21) Appl. No.: 15/166,897

(22) Filed: May 27, 2016

(65) Prior Publication Data

US 2017/0023491 A1    Jan. 26, 2017

Related U.S. Application Data (60) Provisional application No. 62/196,875, filed on Jul. 24, 2015.

(51) Int. Cl.
  *G01N 21/95* (2006.01)
  *G03F 7/20* (2006.01)
  (Continued)

(52) U.S. Cl.
  CPC ....... *G01N 21/9501* (2013.01); *G01N 21/211* (2013.01); *G03F 7/70625* (2013.01);
  (Continued)

(58) Field of Classification Search
  None
  See application file for complete search history.

(56) References Cited

U.S. PATENT DOCUMENTS 6,272,437 B1    8/2001    Woods et al.
6,943,569 B1    9/2005    Pressley et al.
(Continued)

FOREIGN PATENT DOCUMENTS

| WO | 2012170477 A2 | 12/2012 | |
|---|---|---|---|
| WO | 2015023605 A1 | 2/2015 | |
| WO | WO 2016162228 A1 * | 10/2016 | ............. G03F 7/705 |

OTHER PUBLICATIONS

International Search Report dated Sep. 12, 2016, for PCT Application No. PCT/US2016/042629 filed on Jul. 15, 2016 by KLA-Tencor Corporation, 3 pages.

*Primary Examiner* — John C Kuan
(74) *Attorney, Agent, or Firm* — Spano Law Group; Joseph S. Spano (57) ABSTRACT

Methods and systems for evaluating and ranking the measurement efficacy of multiple sets of measurement system combinations and recipes for a particular metrology application are presented herein. Measurement efficacy is based on estimates of measurement precision, measurement accuracy, correlation to a reference measurement, measurement time, or any combination thereof. The automated the selection of measurement system combinations and recipes reduces time to measurement and improves measurement results. Measurement efficacy is quantified by a set of measurement performance metrics associated with each measurement system and recipe. In one example, the sets of measurement system combinations and recipes most capable of measuring the desired parameter of interest are presented to the user in rank order based on corresponding values of one or more measurement performance metrics. A user is able to select the appropriate measurement system combination in an objective, quantitative manner.

22 Claims, 5 Drawing Sheets

(51) Int. Cl.
*G01N 21/21* (2006.01)
*G01B 21/04* (2006.01)

(52) U.S. Cl.
CPC .......... *G03F 7/70633* (2013.01); *G01B 21/04* (2013.01); *G01B 2210/56* (2013.01); *G01N 2021/213* (2013.01); *G03F 7/705* (2013.01)

(56) References Cited

U.S. PATENT DOCUMENTS

| | | | |
|---|---|---|---|
| 6,982,792 | B1 | 1/2006 | Woollam et al. |
| 6,996,492 | B1* | 2/2006 | Testoni .............. G01N 23/2252 378/137 |
| 7,061,614 | B2 | 6/2006 | Wang et al. |
| 7,478,019 | B2 | 1/2009 | Zangooie et al. |
| 7,739,065 | B1 | 6/2010 | Lee et al. |
| 7,933,026 | B2 | 4/2011 | Opsal et al. |
| 8,427,645 | B2 | 4/2013 | Vagos et al. |
| 8,666,703 | B2 | 3/2014 | Ferns et al. |
| 8,843,875 | B2 | 9/2014 | Pandev |
| 2005/0128489 | A1 | 6/2005 | Bao et al. |
| 2010/0118316 | A1 | 5/2010 | Mihaylov et al. |
| 2011/0276935 | A1 | 11/2011 | Fouquet et al. |
| 2011/0307424 | A1* | 12/2011 | Jin ....................... G06N 99/005 706/12 |
| 2012/0224183 | A1* | 9/2012 | Fay ..................... G01B 9/0209 356/491 |
| 2013/0060354 | A1 | 3/2013 | Choi et al. |
| 2013/0132036 | A1* | 5/2013 | Saleh .................. G03F 7/70625 702/189 |
| 2013/0321810 | A1 | 12/2013 | Wang et al. |
| 2014/0347666 | A1 | 11/2014 | Veldman et al. |
| 2015/0058813 | A1 | 2/2015 | Kim et al. |

* cited by examiner

AUTOMATED METROLOGY SYSTEM SELECTION

CROSS REFERENCE TO RELATED APPLICATION

The present application for patent claims priority under 35 U.S.C. § 119 from U.S. provisional patent application Ser. No. 62/196,875, entitled "Fast and Automated Subsystem Recommendation Method for Critical Dimensions Measurement in Semiconductor Process," filed Jul. 24, 2015, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

In response to these challenges, more complex optical tools have been developed. Multiple, different measurement technologies are available, and measurements are performed over a large ranges of several machine parameters (e.g., wavelength, azimuth and angle of incidence, etc.), and often simultaneously. As a result, the measurement time, computation time, and the overall time to generate reliable results, including measurement recipes, increases significantly.

Traditionally, the selection of measurement technique and the associated measurement recipe is performed on a trial-and-error basis. An experienced user manually selects various measurement techniques and recipes and performs an offline analysis to evaluate measurement efficacy. In some examples, measurement results are compared with reference measurement data, e.g., Tunneling Electron Microscope (TEM) data to determine measurement efficacy. In some other examples, a user performs model-based analysis to estimate measurement sensitivity to modelled parameters of interest, measurement precision of the modelled parameters of interest, and parameter correlation among different measurement subsystems. These results guide the user in the final determination of the measurement techniques and associated recipes to be used in a particular measurement application.

Traditional techniques for selecting the appropriate measurement techniques and associated recipes are limited. Model based sensitivity, precision and correlation analysis is limited by the number of points in parameter space that can be simulated in a reasonable period of time. These points may not accurately represent the actual measurement application. In another example, the sensitivity, precision and correlation estimates provide a complex picture of measurement efficacy that is difficult for users to interpret. As a result, it is difficult for a user to select the best measurement techniques and recipes from the simulation data currently provided. This allows the selection process to become reliant on user experience and bias, rather than rigorous analysis. Finally, traditional trial-and-error techniques are limited in the number of subsystems and recipe combinations that can be evaluated in a reasonable period of time. This limitation has become especially critical as the diversity of different measurement systems and recipe options have grown exponentially.

For example, the SpectraShape™ 10 K metrology platform available from KLA-Tencor Corporation, Milpitas, Calif., offers over twenty available measurement subsystems. The platform employs a Rotating Polarizer Spectroscopic Ellipsometry (RPSE) measurement technique with six subsystems having different azimuth angle (AA) and angle of Incidence (AOI) options. In addition, the platform employs a Rotating Polarizer Rotating Compensator (RPRC) Ellipsometry measurement technique with six subsystems having different AA and AOI options. In total, the platform offers more than twenty different subsystems with approximately one million available measurement subsystem and recipe combinations for the measurement of a critical dimension. Using available techniques, it is practically impossible for a user to identify and select the most effective combination of measurement subsystems and associated measurement recipes for a particular measurement application.

As the available range of optical metrology measurement subsystems and associated recipes has increased, so has the complexity of the measurement selection process. Improved methods and tools to streamline the identification and selection of the most effective combinations of measurement subsystems and associated measurement recipes for a particular measurement application are desired.

SUMMARY

Methods and systems for evaluating and ranking the measurement efficacy of multiple sets of measurement system combinations and recipes for a particular metrology application are presented herein. The metrology application includes the measurement of structural and material characteristics (e.g., material composition, dimensional characteristics of structures and films, etc.) associated with different semiconductor fabrication processes. Measurement efficacy is based on estimates of measurement precision, measurement accuracy, correlation to a reference measurement, measurement time, or any combination thereof. By automating the selection of measurement system combinations and recipes, time to measurement result is reduced, while measurement efficacy is improved.

In one aspect, the measurement efficacy of each measurement system and recipe is quantified by a set of measurement performance metrics that are presented to a user. Based on these quantitative metrics, a user is able to select the appropriate measurement system combination without depending on personal experience or whim. In this manner, sets of measurement system combinations and recipes that are most capable of measuring the desired parameter(s) of interest are made available to the user in a ranked order based on one or more measurement performance metrics.

In one example, a measurement model indicative of a measurement of a parameter of interest by a metrology system at a plurality of measurement scenarios is received by an automated measurability ranking (AMR) tool 150. Each measurement scenario includes different values of an angle of incidence, azimuth angle, illumination wavelength, polarization state, or any combination thereof. A model reliability evaluation module 151 of the AMR tool 150 determines a subset of the plurality of measurement scenarios that increases a reliability and sensitivity of the measurement to the parameter of interest.

A Design of Experiments (DOE) generation module 155 of AMR tool 150 determines a set of DOE measurement data associated with a simulation of the measurement for a range of known values of the parameter of interest and the subset of the plurality of measurement scenarios. A DOE tracking analysis module 160 of AMR tool 150 determines estimated values of the parameter of interest based on the set of DOE measurement data corresponding to each of the known values of the parameter of interest. Furthermore, the DOE tracking analysis module 160 of AMR tool 150 determines one or more indications of a difference between the known values of the parameter of interest and the estimated values of the parameter of interest.

A performance metric evaluation module 166 of AMR tool 150 determines one or more measurement performance metrics indicative of the measurement performance of one or more of the measurement scenarios based on the indications of the difference between the known values and the estimated values of the parameter of interest. The performance metric evaluation module 166 communicates the measurement performance metrics to a user.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for evaluating and ranking the measurement efficacy of multiple sets of measurement system combinations and recipes for a particular metrology application are presented herein. The metrology application includes the measurement of structural and material characteristics (e.g., material composition, dimensional characteristics of structures and films, etc.) associated with different semiconductor fabrication processes. Measurement efficacy is based on estimates of measurement precision, measurement accuracy, correlation to a reference measurement, measurement time, or any combination thereof. By automating the selection of measurement system combinations and recipes, time to measurement result is reduced, while measurement efficacy is improved.

In one aspect, the measurement efficacy of each measurement system and recipe is quantified by a set of measurement performance metrics that are presented to a user. Based on these quantitative metrics, a user is able to select the appropriate measurement system combination without depending on personal experience or whim. In this manner, sets of measurement system combinations and recipes that are most capable of measuring the desired parameter(s) of interest are made available to the user in a ranked order based on one or more measurement performance metrics.

Figure 1:
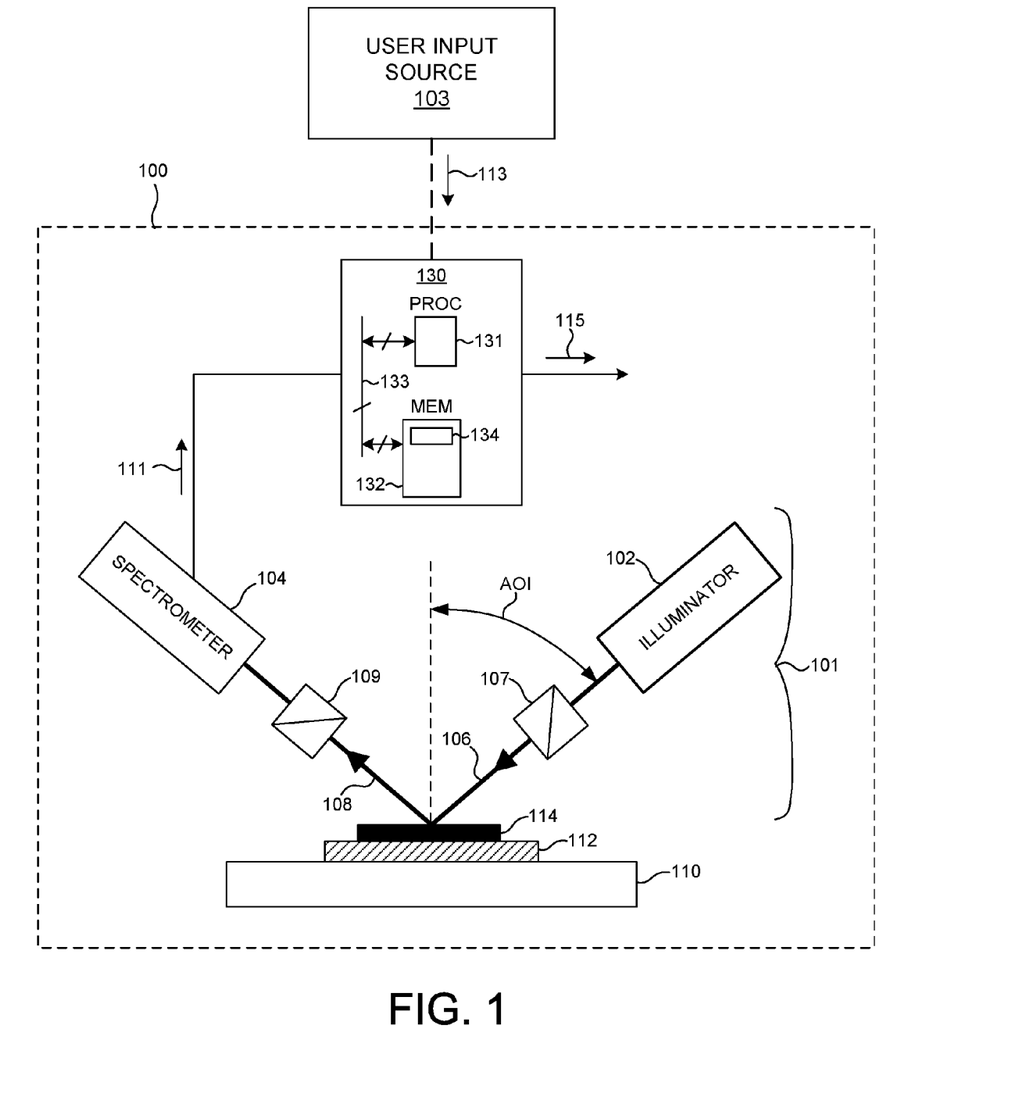
FIG. 1 is a diagram illustrative of a system 100 for measuring characteristics of a semiconductor wafer in accordance with the methods described herein.

FIG. 1 illustrates a system 100 for measuring characteristics of a semiconductor wafer. As shown in FIG. 1, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer 101 equipped with an illuminator 102 and a spectrometer 104. The illuminator 102 of the system 100 is configured to generate and direct illumination of a selected wavelength range (e.g., 120-1700 nm) to the structure 114 disposed on the surface of the semiconductor wafer 112. In turn, the spectrometer 104 is configured to receive light from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis of radiation passed by the analyzer. These spectra 111 are passed to the computing system 130 for analysis of the structure 114.

In a further embodiment, the metrology system 100 is a measurement system 100 that includes one or more computing systems 130 configured to execute an automated measurability ranking (AMR) tool in accordance with the description provided herein. In the preferred embodiment, the AMR tool is a set of program instructions 134 stored in a memory 132. The program instructions 134 are read and executed by one or more processors of computing system 130 to realize measurability ranking functionality as described herein. Computing system 130 may be communicatively coupled to the spectrometer 104. In one aspect, computing system 130 is configured to receive measurement data 111 associated with a measurement (e.g., critical dimension, film thickness, composition, process, etc.) of the structure 114 of specimen 112. In one example, the measurement data 111 includes an indication of the measured spectral response of the specimen by measurement system 100 based on the one or more sampling processes from the spectrometer 104. In some embodiments, computing system 130 is further configured to determine specimen parameter values of structure 114 from measurement data 111. In one example, the computing system 130 is configured to access model parameters in real-time, employing Real Time Critical Dimensioning (RTCD), or it may access libraries of pre-computed models for determining a value of at least one specimen parameter value associated with the target structure 114.

In addition, in some embodiments, computing system 130 is further configured to receive user input 113 from a user input source 103 such as a graphical user interface, keyboard, etc.

In some embodiments, measurement system 100 is further configured to store one or more candidate recipes 115 in a memory (e.g., memory 132 or an external memory).

It should be recognized that the various steps described throughout the present disclosure may be carried out by a single computer system 130 or, alternatively, a multiple computer system 130. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, computing system 130 may be configured to perform any other step(s) of any of the method embodiments described herein.

The computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium. In general, computing system 130 may be integrated with a measurement system such as measurement system 100, or alternatively, may be separate from any measurement system. In this sense, computing system 130 may be remotely located and receive measurement data and user input 113 from any measurement source and user input source, respectively.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Memory 132 storing program instructions 134 may include a computer-readable medium such as a read-only memory, a random access memory, a magnetic or optical disk, or a magnetic tape.

In addition, the computer system 130 may be communicatively coupled to the spectrometer 104 or the illuminator subsystem 102 of the ellipsometer 101, or the user input source 103 in any manner known in the art.

The computing system 130 may be configured to receive and/or acquire data or information from the user input source 103 and subsystems of the system (e.g., spectrometer 104, illuminator 102, and the like) by a transmission medium that may include wireline and/or wireless portions. In this manner, the transmission medium may serve as a data link between the computer system 130, user input source 103, and other subsystems of the system 100. Further, the computing system 130 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system. Moreover, the computer system 130 may send data to external systems via a transmission medium.

The embodiments of the system 100 illustrated in FIG. 1 may be further configured as described herein. In addition, the system 100 may be configured to perform any other block(s) of any of the method embodiment(s) described herein.

In general, ellipsometry is an indirect method of measuring physical properties of the specimen under inspection. In most cases, the measured values (e.g., $\alpha_{meas}$ and $\beta_{meas}$) cannot be used to directly determine the physical properties of the specimen. The nominal measurement process consists of parameterization of the structure (e.g., film thicknesses, critical dimensions, etc.) and the machine (e.g., wavelengths, angles of incidence, polarization angles, etc.). A measurement model is created that attempts to predict the measured values (e.g., $\alpha_{meas}$ and $\beta_{meas}$). As illustrated in equations (1) and (2), the measurement model includes parameters associated with the machine ($P_{machine}$) and the specimen ($P_{specimen}$).

$$\alpha_{model} = f(P_{machine}, P_{specimen}) \quad (1)$$

$$\beta_{model} = g(P_{machine}, P_{specimen}) \quad (2)$$

Machine parameters are parameters used to characterize the metrology tool (e.g., ellipsometer 101). Exemplary machine parameters include angle of incidence (AOI), analyzer angle ($A_0$), polarizer angle ($P_0$), illumination wavelength, numerical aperture (NA), etc. Specimen parameters are parameters used to characterize the specimen (e.g., specimen 112 including structures 114). For a thin film specimen, exemplary specimen parameters include refractive index, dielectric function tensor, nominal layer thickness of all layers, layer sequence, etc. For measurement purposes, the machine parameters are treated as known, fixed parameters and one or more of the specimen parameters are treated as unknown, floating parameters.

In some examples, the floating parameters are resolved by an iterative process (e.g., regression) that produces the best fit between theoretical predictions and experimental data. The unknown specimen parameters, $P_{specimen}$, are varied and the model output values (e.g., $\alpha_{model}$ and $\beta_{model}$) are calculated until a set of specimen parameter values are determined that results in a close match between the model output values and the experimentally measured values (e.g., $\alpha_{meas}$ and $\beta_{meas}$). In a model based measurement application such as spectroscopic ellipsometry on a CD specimen, a regression process (e.g., ordinary least squares regression) is employed to identify specimen parameter values that minimize the differences between the model output values and the experimentally measured values for a fixed set of machine parameter values.

In some examples, the floating parameters are resolved by a search through a library of pre-computed solutions to find the closest match. In a model based measurement application such as spectroscopic ellipsometry on a CD specimen, a library search process is employed to identify specimen parameter values that minimize the differences between pre-computed output values and the experimentally measured values for a fixed set of machine parameter values.

In a model-based measurement application, simplifying assumptions often are required to maintain sufficient throughput. In some examples, the truncation order of a Rigorous Coupled Wave Analysis (RCWA) must be reduced to minimize compute time. In another example, the number or complexity of library functions is reduced to minimize search time. These simplifying assumptions may lead to unacceptable errors in the estimation of measurement parameter values. The specification of these simplifying assumptions is part of the measurement recipe associated with a particular measurement system selected to perform a particular measurement.

Figure 2:
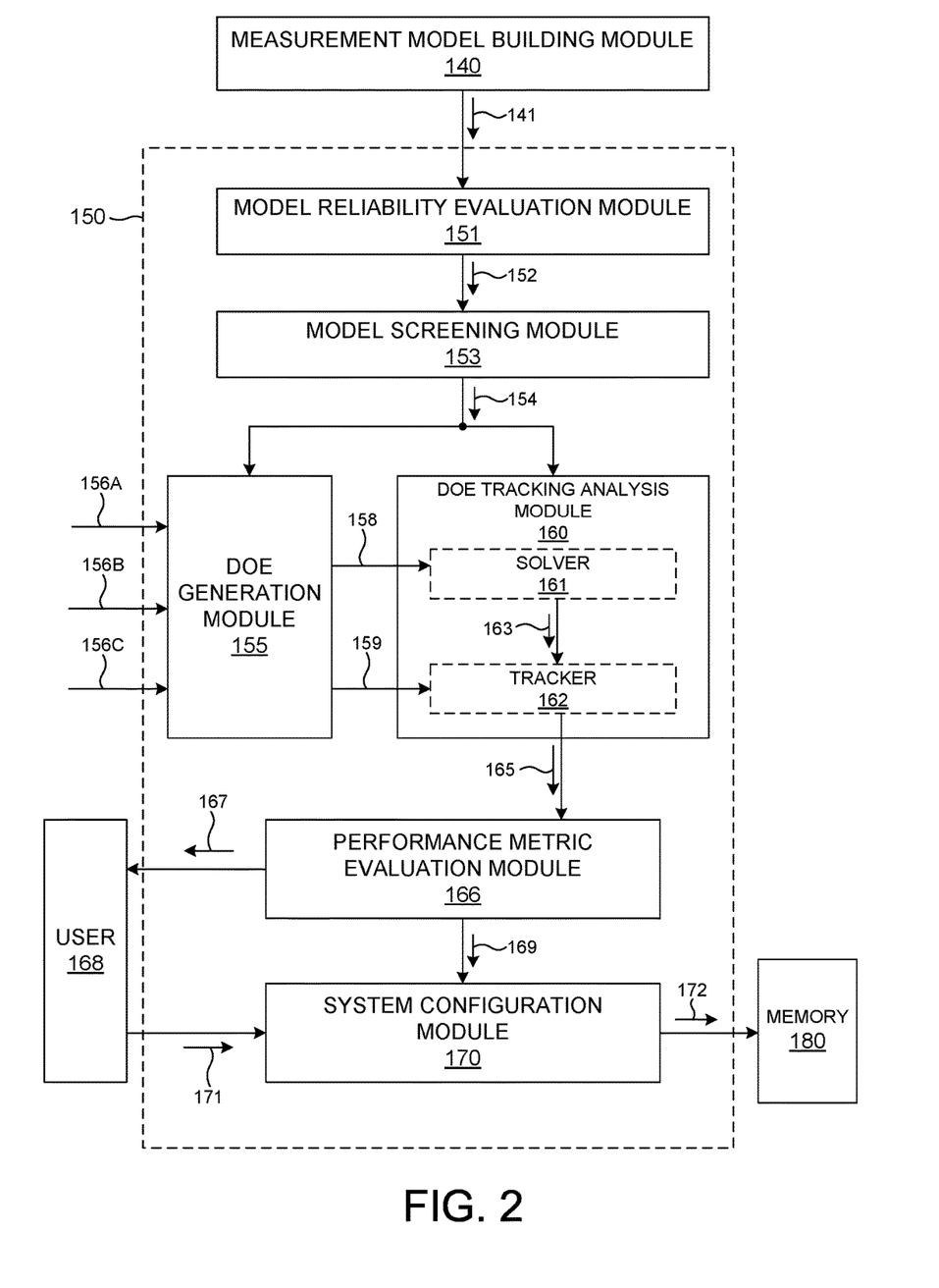
FIG. 2 is a diagram illustrative of an exemplary AMR tool 150 implemented by computing system 130 depicted in FIG. 1.

FIG. 2 is a diagram illustrative of an exemplary AMR tool 150 implemented by computing system 130. In the embodiment depicted in FIG. 2, computing system 130 is configured to implement automated measurability ranking functionality as described herein.

In the embodiment depicted in FIG. 2, a measurement model building module 140 is employed to generate a measurement model 141 of a structure to be measured by a particular measurement system. Model based optical measurement of critical dimensions (CDs), thin film thicknesses, optical properties and material compositions, overlay, lithography focus/dose, etc., typically requires a geometric model of the underlying structure to be measured. Thus, a measurement model includes the physical dimensions, material properties, and parameterization of the structure. In some embodiments, measurement model building module 140 reads a file that contains equations representative of the geometric features of the structure to be measured. In some embodiments, this file is generated by a lithography simulator such as PROLITH software available from KLA-Tencor Corporation, Milpitas, Calif. (USA). The measurement model building module 140 sets the parameterization and constraints of the measurement model 141 based on this application information.

Measurement model 141 generated by measurement model building module 140 includes machine parameter values and specimen parameter values. Depending on the measurement system under consideration, various machine parameters and ranges of machine parameter values are available for measurement. In one example, the SpectraShape™ 10 K metrology tool available from KLA-Tencor, Corporation, Milpitas, Calif. (USA), offers three different angles of incidence, an arbitrary selection of azimuth angle, selectable wavelength range, and more than one collection angle.

A measurement recipe for a particular measurement system includes a selection of available machine parameters. In some examples, a metrology tool includes multiple, different metrology subsystems (e.g., spectroscopic ellipsometry and spectroscopic reflectometry). A measurement scenario defines a measurement of a metrology target performed by a particular measurement system in accordance with a particular measurement recipe. AMR tool 150 is employed to define and rank one or more available measurement scenarios for the measurement of one or more parameters of interest.

As depicted in FIG. 2, one or more different measurement models 141 are received by AMR tool 150. Each measurement model 141 is received and evaluated by model reliability evaluation module 151 of AMR tool 150. To accurately evaluate the measurability of parameters of interest with different measurement systems and recipes, a stable measurement model is essential.

In one example, model reliability evaluation module 151 confirms that the geometric features of the measurement model are physically consistent with the process employed to create the features.

In another example, model reliability evaluation module 151 evaluates measurement signal values predicted by the measurement model for a range of values of each parameter of interest. In one example, spectroscopic ellipsometry (SE) signals are averaged over a range of illumination wavelengths for each value in a range of values of a parameter of interest. The averaged SE signals are evaluated to confirm that the averaged signals are non-zero for each possible value within the range of values of the parameter of interest. In addition, the SE signals are evaluated to confirm that data exists for each possible value within the range of values of the parameter of interest. If no data exists for one or more possible values of the parameter of interest, this is indicative of a failure of the measurement model.

In another example, model reliability evaluation module 151 evaluates the first derivative of measurement signal values predicted by the measurement model with respect to each parameter of interest for a range of values of each parameter of interest. In the SE example, described above, the first derivative of the averaged SE signals should be continuous throughout the range of values of the parameter of interest. In addition it is preferable that the derivative of the averaged SE signals over the range of parameter values should be smooth and non-zero valued. Ranges of parameter values that correspond with non-smooth or discontinuous derivatives are excluded from further consideration by model reliability evaluation module 151.

Non-smooth or discontinuous first derivatives may be identified in a number of different ways. In one example, model reliability evaluation module 151 evaluates the second derivative of the measurement signal values predicted by the measurement model for a range of values of each parameter of interest. In the SE example, described above, the second derivative of the averaged SE signals should be below a predetermined threshold value throughout the range of values of the parameter of interest. Ranges of parameter values that correspond with second derivatives that exceed a predetermined threshold value are excluded from further consideration by model reliability evaluation module 151.

In another example, model reliability evaluation module 151 performs a polynomial fit to the first derivative of the measurement signal values with respect to a parameter of interest over a local range of values of the parameter of interest. If the fit quality is poor, (e.g., goodness of fit parameter <0.9), then the corresponding local range of parameter values is excluded from further consideration by model reliability evaluation module 151.

In another example, model reliability evaluation module 151 performs a polynomial fit to the first derivative of the measurement signal values at a set of wavelengths with respect to a parameter of interest over a local range of values of the parameter of interest. If the fit quality is poor over a particular wavelength range, (e.g., goodness of fit parameter <0.9), then the measurement signal corresponding to the particular wavelength range is excluded from further consideration by model reliability evaluation module 151.

In another example, model reliability evaluation module 151 evaluates statistics (e.g., three-sigma values, four-sigma values, etc.) associated with the first derivative of measurement signal values predicted by the measurement model with respect to each parameter of interest for a range of values of each parameter of interest. If the statistical measures indicate broad variance, then the corresponding range of parameter values is excluded from further consideration by model reliability evaluation module 151.

After evaluation by model reliability evaluation module 151, any constraints on ranges of parameters of interest or machine parameters identified by model reliability evaluation module 151 are implemented in measurement model 152. Thus, if no constraints are identified by model reliability evaluation module 151, then measurement model 152 is the same as measurement model 141. However, if constraints are identified by model reliability evaluation module 151, then measurement model 152 is a constrained version of measurement model 141 having a reduced set (i.e., subset) of available machine parameter values.

The measurement model 152 is received and evaluated by model screening module 153 of AMR tool 150. Model screening module 153 performs precision analysis, sensitivity analysis, or a combination thereof. Based on these analyses, measurement subsystems and ranges of machine parameters are selected that are capable of performing a measurement of a parameter of interest with the requisite precision. In one example, a Rotating Polarizer Spectroscopic Ellipsometry (RPSE) system includes a range of available azimuth angles between zero degrees and three hundred sixty degrees. In this example, model screening module calculates measurement signal sensitivity to changes in a parameter of interest for a range of azimuth angles between zero degrees and three hundred sixty degrees. One or more azimuth angles are selected that provide the highest measurement sensitivity to the parameter of interest. In a similar manner, a range of azimuth angles are evaluated for a Rotating Polarizer Rotating Compensator (RPRC) system.

After evaluation by model screening module 153, any constraints on ranges of machine parameters identified by model screening module 153 are implemented in measurement model 154.

Design of Experiments (DOE) generation module 155 receives measurement model 154 and generates a set of synthetic Design of Experiment (DOE) measurement data 158 for different values of a parameter of interest and machine parameter values based on simulations of the measurement model 154 under consideration. For spectral measurements, each DOE spectra of the set of DOE spectra 158 includes simulated spectral measurement data associated with a measurement of a particular parameter of interest at a particular value for a particular measurement recipe (e.g., set of machine parameter values) under consideration. In some examples, the simulation of the DOE spectra includes a noise definition 156A, a system parameter perturbation 156B, a fixed parameter perturbation 156C, or any combination thereof. Both the known values of the parameter of interest under consideration 159 and the associated set of DOE spectra 158 are provided to DOE tracking analysis module 160.

DOE tracking analysis module 160 performs a regression analysis on each DOE spectra of the set of DOE spectra 158 using an electromagnetic solver 161. The regression analysis determines an estimated value 163 of a parameter of interest under consideration for each DOE spectra.

The estimated values 163 of the parameter of interest are compared to the known values of the parameter of interest 159 by tracker 162. Differences between the estimated values 163 and known values 159 highlight the noise rejection capability and robustness of each measurement system and recipe 164 under consideration.

Figure 3:
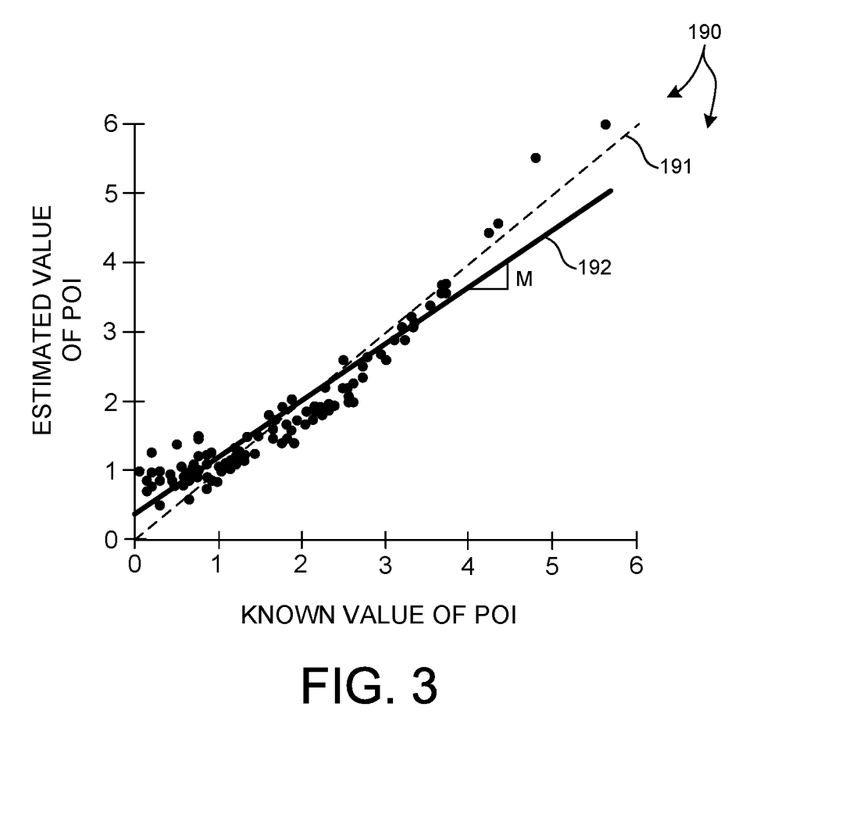
FIG. 3 depicts a plot 190 of estimated values and corresponding known values of a parameter of interest.

FIG. 3 depicts a plot 190 of estimated values of a parameter of interest (POI) and corresponding known values of the parameter of interest. If the estimated values of the parameter of interest perfectly matched the corresponding known values, all points would lie on line 191. In reality, there are discrepancies. Line 192 represents a linear fit to the data points.

In some examples, tracker 162 quantifies the measurement accuracy as the 3G value of the difference between the estimated value of the parameter of interest 163 and the known value of the parameter of interest 159 for each measurement scenario. In one example, accuracy is defined by equations (1)-(3), where the estimated value of the parameter of interest is denoted a $y_{est_i}$ and the known value of the parameter of interest is denoted as $y_{known_i}$.

$$\text{Accuracy} = 3\sigma = 3\sqrt{\frac{1}{N}\sum_{i=1}^{N} e_i - \overline{e}} \quad (3)$$

$$\overline{e} = \frac{1}{N}\sum_{i=1}^{N} e_i \quad (4)$$

$$e_i = y_{est_i} - y_{known_i} \quad (5)$$

In some examples, tracker 162 determines the slope of the regression line of the data points (e.g., line 192 depicted in FIG. 3).

In some examples, tracker 162 determines the $R^2$ value (i.e., coefficient of determination) associated with the differences between the estimated values of the parameter of interest 163 and the known values of the parameter of interest 159. The range of $R^2$ values is between zero and one, with one being a perfect fit between the estimated values of the parameter of interest 163 and the known values of the parameter of interest 159 for each measurement scenario. In some examples, the $R^2$ value is calculated as illustrated in equation (6).

$$R^2 = 1 - \frac{\sum_{i=1}^{N} e_i^2}{\frac{1}{N}\sum_{i=1}^{N} y_{est_i}} \quad (6)$$

The accuracy, slope, and R2 results 165 determined by DOE tracking analysis module 160 are received by performance metric evaluation module 166. Performance metric evaluation module 166 generates aggregate, quantitative metrics based on the results of the DOE tracking analysis performed by DOE tracking analysis module 160.

In one example, performance metric evaluation module 166 generates a measurability score for each parameter of interest from the tracking results generated by DOE tracking analysis module 160 over the range of measurement scenarios under consideration. The measurability score, Mscore, depends on accuracy, slope, and R2 values associated with each parameter of interest as illustrated by equations (7)-(10), where $\Delta=0.005$ and $\gamma=0.3$.

$$M_{score} = \left(\frac{aCorr}{1+\Delta}\right)^{\left(\frac{1+\Delta}{aGOF+\Delta}\right)^2} \quad (7)$$

$$aGOF = \left(\prod_{i=1}^{N} GOF_i\right)^{\left(\frac{1}{N}\right)} \quad (8)$$

$$GOF = 1 - \frac{2}{\pi}\tan^{-1}\sqrt{\frac{Accuracy^2}{\gamma^2}} \quad (9)$$

$$aCorr = \left(\prod_{i=1}^{N} abs(1 - abs(Slope_i - 1))\right)^{\frac{1}{N}} \cdot \left(\prod_{i=1}^{N} abs(1 - R_i^2)\right)^{\frac{1}{N}} \quad (10)$$

The multiplicative nature of the calculations underlying the measurability score, $M_{score}$, implies that all values of a parameter of interest must be measurable to make the value of measurability reasonable.

In another example, performance metric evaluation module 166 generates an R-score evaluated for each parameter of interest. The R-score is determined based on accuracy, slope, and the $R^2$ value.

An overall R-score, $Rscore_{total}$, is determined based on a weighted average of the R-scores for each individual parameter of interest as illustrated by equation (11).

$$Rscore_{total} = \sum_{i=1}^{N} W_{R_i} * R_{score_i} \quad (11)$$

For each parameter of interest, i, an R-score is determined by equations (12)-(14).

$$Rscore_i = Ce^{-\frac{slope_{norm}^2}{2}} \frac{R^2}{1+\Delta}\left(\frac{1+\Delta}{GOF+\Delta}\right)^2 \quad (12)$$

where C=100, $\Delta$=0.005, $$slope_{norm} = \frac{slope - \mu}{\sigma} \quad (13)$$

where $\mu$=1.0 and $\sigma$=0.025, and $$GOF = 1 - \frac{2}{\pi}\tan^{-1}\sqrt{\frac{Accuracy^2}{\gamma^2}} \quad (14)$$

where $\gamma$=0.3

The R-score ranges from zero to one hundred, with 100 being perfect and zero being least capable.

The additive nature of the overall R-score metric provides additional information by balancing the measurement capability of a particular measurement scenario for the measurement of multiple parameters of interest.

Equations (11)-(14) are provided by way of non-limiting example, as many other formulations of the R-score metric may be contemplated within the scope of this patent document.

Figure 4:
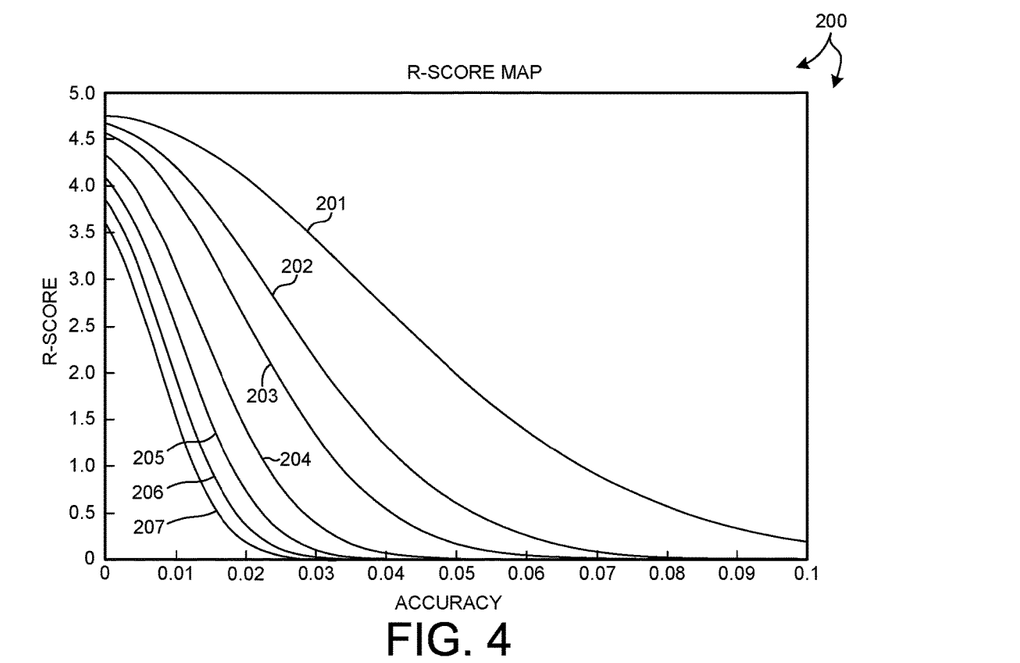
FIG. 4 depicts a plot 200 illustrating a simulated example of the changes in the value of the R-Score with accuracy for various R2 values.

FIG. 4 depicts a plot 200 illustrating a simulated example of the changes in the value of the R-Score with accuracy for various $R^2$ values. Plotline 201 depicts the R-score values as a function of accuracy for an $R^2$ value of 0.99. Plotline 202 depicts the R-score values as a function of accuracy for an $R^2$ value of 0.97. Plotline 203 depicts the R-score values as a function of accuracy for an $R^2$ value of 0.95. Plotline 204 depicts the R-score values as a function of accuracy for an $R^2$ value of 0.90. Plotline 205 depicts the R-score values as a function of accuracy for an $R^2$ value of 0.85. Plotline 206 depicts the R-score values as a function of accuracy for an $R^2$ value of 0.80. Plotline 207 depicts the R-score values as a function of accuracy for an $R^2$ value of 0.75. As depicted in FIG. 4, the R-score value increases as accuracy improves, and the R-score value increases as the $R^2$ value increases.

Figure 5:
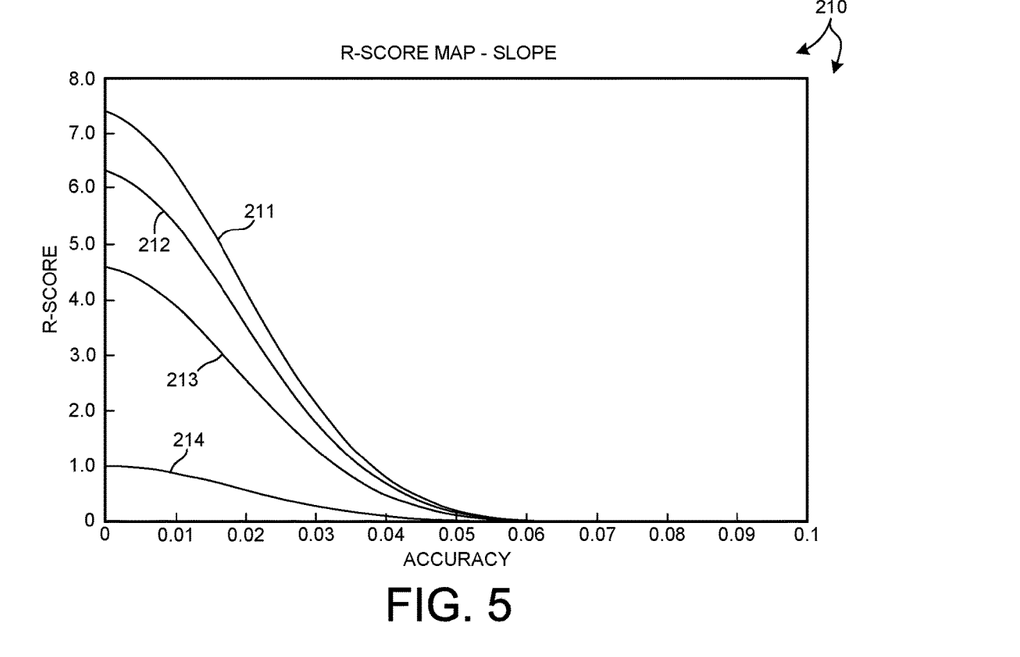
FIG. 5 depicts a plot 210 illustrating a simulated example of the changes in the value of the R-Score with accuracy for various slope values.

FIG. 5 depicts a plot 210 illustrating a simulated example of the changes in the value of the R-Score with accuracy for various slope values. Plotline 211 depicts the R-score values as a function of accuracy for a slope value of 0.99. Plotline 212 depicts the R-score values as a function of accuracy for a slope value of 0.97. Plotline 213 depicts the R-score values as a function of accuracy for a slope value of 0.95. Plotline 214 depicts the R-score values as a function of accuracy for a slope value of 0.90. As depicted in FIG. 5, the R-score value increases as accuracy improves, and the R-score value increases as the slope increases (approaches a value of one). The R-Score is very sensitive (i.e., dramatically decreases) when the slope is less than 0.9.

In yet another example, performance metric evaluation module 166 generates a T-score. The T-score is defined as the R-score scaled with throughput. The higher the throughput the larger T-score for a given R-score. The T-score metric is important as throughput is one of the most issues in a production environment.

$$Tscore_i = T_i R_{score_i} \quad (15)$$

An overall T-score, $Tscore_{total}$, is determined based on a weighted average of the T-scores for each individual parameter of interest.

$$Tscore_{total} = \sum_{i=1}^{N} W_{T_i} * T_{score_i} \quad (16)$$

The definitions of measurability, R-Score, and T-Score are not unique. In this sense, different formulations of the underlying tracking data may be contemplated within the scope of this patent document. However, it is important that the function value changes monotonically to provide a quantitative evaluation of the measurement capability of each measurement scenario.

In some embodiments, performance metric evaluation module 166 compiles a number of measurement scenarios and associated measurement recipes 169, ranks them based on the measurability score, R-score, and T-score, and communicates them to a user 168. For example, the quantitative performance metrics 167 determined by performance metric evaluation module 166 are presented to a user 168, for example, in ranked order on a display (e.g., computer monitor, etc.).

System configuration module 170 receives an indication 171 of a selection of one or more measurement scenarios by user 168. In some other examples, a user may interact with a graphical user interface (GUI) that allows a user to select one or more measurement scenarios based on the ranking provided by AMR tool 150.

In response the system configuration module 170 automatically generates the appropriate constraints to the measurement model and measurement system to realize the selected measurement scenario. In some embodiments, the selected measurement scenario configuration 172 is stored in a memory (e.g. memory 180). The stored measurement scenario configurations may be exported to other measurement systems to define measurement scenarios on other systems.

Figure 6:
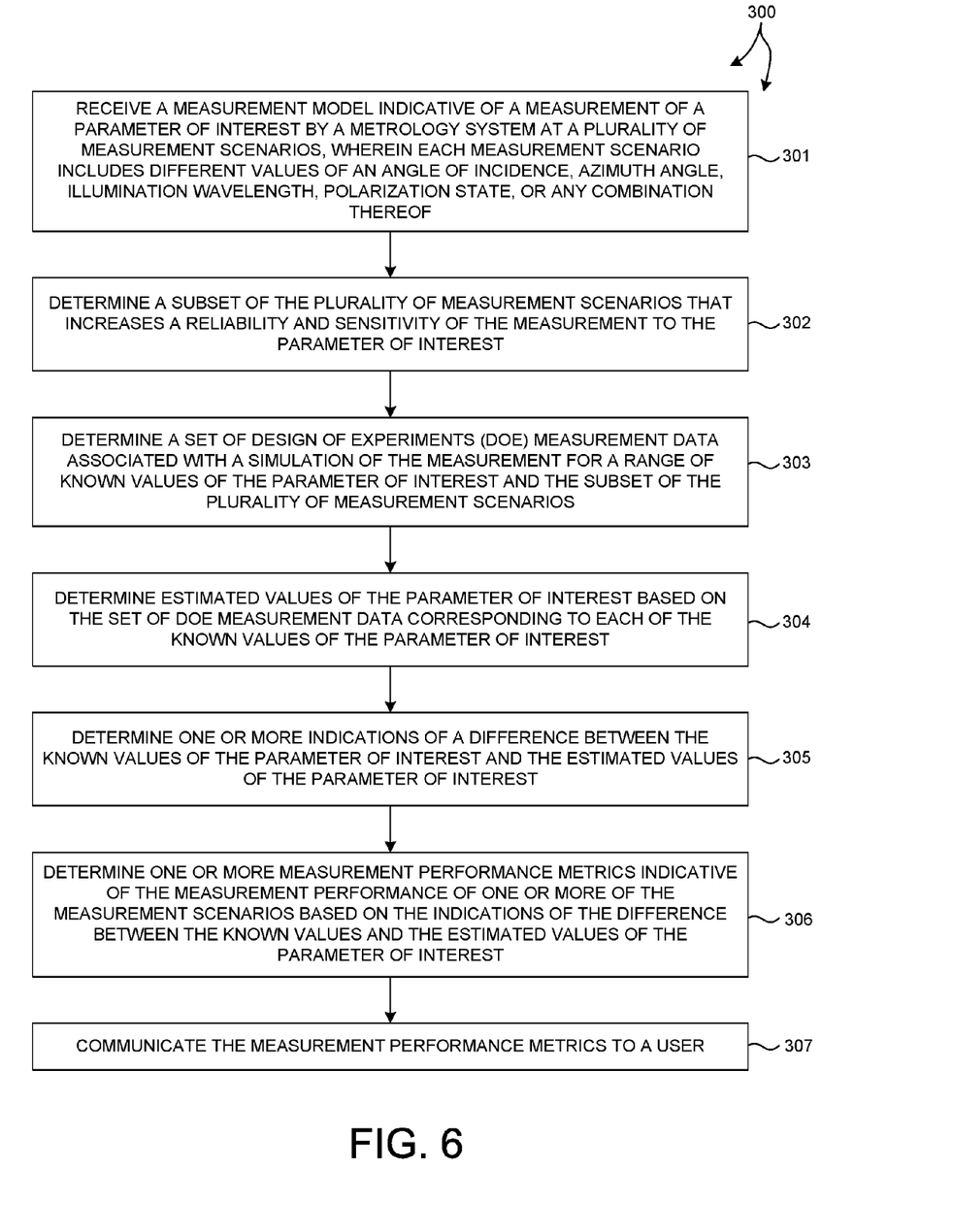
FIG. 6 illustrates a method 300 for evaluating and ranking the measurement efficacy of multiple sets of measurement system combinations and recipes for a particular metrology application in at least one novel aspect.

FIG. 6 illustrates a method 300 for evaluating and ranking the measurement efficacy of multiple sets of measurement system combinations and recipes for a particular metrology application in at least one novel aspect. Method 300 is suitable for implementation by a metrology system such as metrology system 100 illustrated in FIG. 1 of the present invention. In one aspect, it is recognized that data processing blocks of method 300 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 301, a measurement model indicative of a measurement of a parameter of interest by a metrology system at a plurality of measurement scenarios is received by an automated measurability ranking (AMR) tool 150. Each measurement scenario includes different values of an angle of incidence, azimuth angle, illumination wavelength, polarization state, or any combination thereof.

In block 302, a model reliability evaluation module 151 of the AMR tool 150 determines a subset of the plurality of measurement scenarios that increases a reliability and sensitivity of the measurement to the parameter of interest.

In block 303, a Design of Experiments (DOE) generation module 155 of AMR tool 150 determines a set of DOE measurement data associated with a simulation of the measurement for a range of known values of the parameter of interest and the subset of the plurality of measurement scenarios.

In block 304, a DOE tracking analysis module 160 of AMR tool 150 determines estimated values of the parameter of interest based on the set of DOE measurement data corresponding to each of the known values of the parameter of interest.

In block 305, the DOE tracking analysis module 160 of AMR tool 150 determines one or more indications of a difference between the known values of the parameter of interest and the estimated values of the parameter of interest.

In block 306, a performance metric evaluation module 166 of AMR tool 150 determines one or more measurement performance metrics indicative of the measurement performance of one or more of the measurement scenarios based on the indications of the difference between the known values and the estimated values of the parameter of interest.

In block 307, the performance metric evaluation module 166 communicates the measurement performance metrics to a user.

Although the methods discussed herein are explained with reference to system 100, any optical metrology system configured to illuminate and detect light reflected, transmitted, or diffracted from a specimen may be employed to implement the exemplary methods described herein. Exemplary systems include an angle-resolved reflectometer, a scatterometer, a reflectometer, an ellipsometer, a spectroscopic reflectometer or ellipsometer, a beam profile reflectometer, a multi-wavelength, two-dimensional beam profile reflectometer, a multi-wavelength, two-dimensional beam profile ellipsometer, a rotating compensator spectroscopic ellipsometer, etc. By way of non-limiting example, an ellipsometer may include a single rotating compensator, multiple rotating compensators, a rotating polarizer, a rotating analyzer, a modulating element, multiple modulating elements, or no modulating element.

It is noted that the output from a source and/or target measurement system may be configured in such a way that the measurement system uses more than one technology. In fact, an application may be configured to employ any combination of available metrology sub-systems within a single tool, or across a number of different tools.

A system implementing the methods described herein may also be configured in a number of different ways. For example, a wide range of wavelengths (including visible, ultraviolet, infrared, and X-ray), angles of incidence, states of polarization, and states of coherence may be contemplated. In another example, the system may include any of a number of different light sources (e.g., a directly coupled light source, a laser-sustained plasma light source, etc.). In another example, the system may include elements to condition light directed to or collected from the specimen (e.g., apodizers, filters, etc.).

The invention presented herein addresses the problem of determining which combinations of hardware configurations and associated measurement recipes are mse capable of measuring certain semiconductor structural and material characteristics. In many cases, this problem is intractable without the aid of the methods and systems described herein. Moreover, the method described in this invention is not limited to the hardware and/or optical configuration summarized above.

In the field of semiconductor metrology, a metrology system may comprise an illumination system which illuminates a target, a collection system which captures relevant information provided by the illumination system's interaction (or lack thereof) with a target, device or feature, and a processing system which analyzes the information collected using one or more algorithms. Metrology tools can be used to measure structural and material characteristics (e.g, material composition, dimensional characteristics of structures and films such as film thickness and/or critical dimensions of structures, overlay, etc.) associated with various semiconductor fabrication processes. These measurements are used to facilitate process controls and/or yield efficiencies in the manufacture of semiconductor dies.

A metrology system can comprise one or more hardware configurations which may be used in conjunction with certain embodiments of this invention to, e.g., measure the various aforementioned semiconductor structural and material characteristics. Examples of such hardware configurations include, but are not limited to, the following: a spectroscopic ellipsometer (SE), a SE with multiple angles of illumination, a SE measuring Mueller matrix elements (e.g. using rotating compensator(s)), a single-wavelength ellipsometer, a beam profile ellipsometer (angle-resolved ellipsometer), a beam profile reflectometer (angle-resolved reflectometer), a broadband reflective spectrometer (spectroscopic reflectometer), a single-wavelength reflectometer, an angle-resolved reflectometer, an imaging system, and a scatterometer (e.g. speckle analyzer).

The hardware configurations can be separated into discrete operational systems. On the other hand, one or more hardware configurations can be combined into a single tool. One example of such a combination of multiple hardware configurations into a single tool is described in U.S. Pat. No. 7,933,026, which is hereby incorporated by reference in its entirety for all purposes. In many cases, multiple metrology tools are used for measurements on single or multiple metrology targets. This is described, e.g. in by Zangooie et al., in U.S. Pat. No. 7,478,019, which is hereby incorporated by reference in its entirety for all purposes.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), a displacement between two or more structures (e.g., overlay displacement between overlaying grating structures, etc.), and a dispersion property value of a material used in the structure or part of the structure. Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., a metrology system or a lithography system) that may be used for processing a specimen. The term "specimen" is used herein to refer to a site, or sites, on a wafer, a reticle, or any other sample that may be processed (e.g., printed or inspected for defects) by means known in the art. In some examples, the specimen includes a single site having one or more measurement targets whose simultaneous, combined measurement is treated as a single specimen measurement or reference measurement. In some other examples, the specimen is an aggregation of sites where the measurement data associated with the aggregated measurement site is a statistical aggregation of data associated with each of the multiple sites. Moreover, each of these multiple sites may include one or more measurement targets associated with a specimen or reference measurement.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned". For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
one or more computer systems configured to:
receive a measurement model indicative of a measurement of a parameter of interest by a metrology system at a plurality of measurement scenarios, wherein each of the plurality of measurement scenarios includes different values of an angle of incidence, azimuth angle, illumination wavelength, polarization state, or any combination thereof;
determine a subset of the plurality of measurement scenarios that increases a reliability and sensitivity of the measurement to the parameter of interest;
determine a set of Design of Experiments (DOE) measurement data associated with a simulation of the measurement for a range of known values of the parameter of interest and the subset of the plurality of measurement scenarios;

estimate values of the parameter of interest by solving a measurement model on the set of DOE measurement data corresponding to each of the known values of the parameter of interest;

determine one or more indications of a difference between the known values of the parameter of interest and the estimated values of the parameter of interest;

determine one or more measurement performance metrics indicative of the measurement performance of one or more of the subset of the plurality of measurement scenarios based on the indications of the difference between the known values and the estimated values of the parameter of interest;

communicate the measurement performance metrics to a user;

receive an indication of a selection of a measurement scenario by the user;

generate a measurement system configuration based on the selection; and an illumination source configured to provide an amount of illumination light to one or more metrology targets in accordance with the measurement system configuration; and a detector configured to receive an amount of collected light from the one or more metrology targets in response to the amount of illumination light in accordance with the measurement system configuration.

2. The metrology system of claim 1, wherein the determining the subset of the plurality of measurement scenarios that increases the reliability and sensitivity of the measurement involves eliminating one or more measurement scenarios that result in a discontinuity in a measurement signal response for one or more values of the parameter of interest.

3. The metrology system of claim 1, wherein the determining the subset of the plurality of measurement scenarios that increases the reliability and sensitivity of the measurement involves eliminating one or more measurement scenarios that result in a discontinuity of a derivative of a measurement signal response for one or more values of the parameter of interest.

4. The metrology system of claim 1, wherein the determining the subset of the plurality of measurement scenarios that increases the reliability and sensitivity of the measurement involves fitting a polynomial function to a first derivative of a measurement signal response with respect to a parameter of interest at a set of wavelengths, and excluding measurement signals corresponding to a particular wavelength range if a quality of fit is less than a predetermined threshold value over the particular wavelength range.

5. The metrology system of claim 1, wherein the one or more measurement performance metrics comprise an overall R-score value that is a weighted sum of R-score values associated with each known value of the parameter of interest.

6. The metrology system of claim 1, wherein the one or more measurement performance metrics comprise an overall measurability value that is a product of measurability values associated with each known value of the parameter of interest.

7. The metrology system of claim 5, wherein the one or more measurement performance metrics comprise an overall T-score value that is a weighted sum of T-score values associated with each known value of the parameter of interest, wherein each of the T-score values is a product of the R-score value corresponding to each measurement scenario of the one or more of the subset of the plurality of measurement scenarios and a corresponding indication of a measurement time associated with each measurement scenario.

8. The metrology system of claim 1, wherein the illumination source and the detector are elements of any of a spectroscopic ellipsometer, a spectroscopic reflectometer, a single wavelength ellipsometer, and a beam profile reflectometer.

9. An automated measurability ranking tool comprising computer-readable instructions stored on a non-transitory, computer-readable medium, the computer-readable instructions comprising:

code for causing a computing system to receive a measurement model indicative of a measurement of a parameter of interest by a metrology system at a plurality of measurement scenarios, wherein each of the plurality of measurement scenarios includes different values of an angle of incidence, azimuth angle, illumination wavelength, polarization state, or any combination thereof;

code for causing the computing system to determine a subset of the plurality of measurement scenarios that increases a reliability and sensitivity of the measurement to the parameter of interest;

code for causing the computing system to determine a set of Design of Experiments (DOE) measurement data associated with a simulation of the measurement for a range of known values of the parameter of interest and the subset of the plurality of measurement scenarios;

code for causing the computing system to estimate values of the parameter of interest by solving a measurement model on the set of DOE measurement data corresponding to each of the known values of the parameter of interest;

code for causing the computing system to determine one or more indications of a difference between the known values of the parameter of interest and the estimated values of the parameter of interest;

code for causing the computing system to determine one or more measurement performance metrics indicative of the measurement performance of one or more of the subset of the plurality of measurement scenarios based on the indications of the difference between the known values and the estimated values of the parameter of interest;

code for causing the computing system to communicate the measurement performance metrics to a user;

code for causing the computing system to receive an indication of a selection of a measurement scenario by the user;

code for causing the computing system to generate a measurement system configuration based on the selection; and code for causing the computing system to perform a measurement based on the measurement system configuration.

10. The automated measurability ranking tool of claim 9, wherein the determining the subset of the plurality of measurement scenarios that increases the reliability and sensitivity of the measurement involves eliminating one or more measurement scenarios that result in a discontinuity in a measurement signal response for one or more values of the parameter of interest.

11. The automated measurability ranking tool of claim 9, wherein the determining the subset of the plurality of measurement scenarios that increases the reliability and sensitivity of the measurement involves eliminating one or more measurement scenarios that result in a discontinuity of a derivative of measurement signal response for one or more values of the parameter of interest.

12. The automated measurability ranking tool of claim 9, wherein the determining the subset of the plurality of measurement scenarios that increases the reliability and sensitivity of the measurement involves fitting a polynomial function to a first derivative of a measurement signal response with respect to a parameter of interest at a set of wavelengths, and excluding measurement signals corresponding to a particular wavelength range if a quality of fit is less than a predetermined threshold value over the particular wavelength range.

13. The automated measurability ranking tool of claim 9, wherein the one or more measurement performance metrics comprise an overall R-score value that is a weighted sum of R-score values associated with each known value of the parameter of interest.

14. The automated measurability ranking tool of claim 9, wherein the one or more measurement performance metrics comprise an overall measurability value that is a product of measurability values associated with each known value of the parameter of interest.

15. The automated measurability ranking tool of claim 13, wherein the one or more measurement performance metrics comprise an overall T-score value that is a weighted sum of T-score values associated with each known value of the parameter of interest, wherein each of the T-score values is a product of the R-score value corresponding to each measurement scenario of the one or more of the subset of the plurality of measurement scenarios and a corresponding indication of a measurement time associated with each measurement scenario.

16. A method comprising:
receiving a measurement model indicative of a measurement of a parameter of interest by a metrology system at a plurality of measurement scenarios, wherein each of the plurality of measurement scenarios includes different values of an angle of incidence, azimuth angle, illumination wavelength, polarization state, or any combination thereof;
determining a subset of the plurality of measurement scenarios that increases a reliability and sensitivity of the measurement to the parameter of interest;
determining a set of Design of Experiments (DOE) measurement data associated with a simulation of the measurement for a range of known values of the parameter of interest and the subset of the plurality of measurement scenarios;
estimating values of the parameter of interest by solving a measurement model on the set of DOE measurement data corresponding to each of the known values of the parameter of interest;
determining one or more indications of a difference between the known values of the parameter of interest and the estimated values of the parameter of interest;
determining one or more measurement performance metrics indicative of the measurement performance of one or more of the subset of the plurality of measurement scenarios based on the indications of the difference between the known values and the estimated values of the parameter of interest;
communicating the measurement performance metrics to a user;
receiving an indication of a selection of a measurement scenario by the user;
generating a measurement system configuration based on the selection; and
performing a measurement based on the measurement system configuration.

17. The method of claim 16, wherein the determining the subset of the plurality of measurement scenarios that increases the reliability and sensitivity of the measurement involves eliminating one or more measurement scenarios that result in a discontinuity in a measurement signal response for one or more values of the parameter of interest.

18. The method of claim 16, wherein the determining the subset of the plurality of measurement scenarios that increases the reliability and sensitivity of the measurement involves eliminating one or more measurement scenarios that result in a discontinuity of a derivative of measurement signal response for one or more values of the parameter of interest.

19. The method of claim 16, wherein the one or more measurement performance metrics comprise an overall R-score value that is a weighted sum of R-score values associated with each known value of the parameter of interest.

20. The method of claim 16, wherein the one or more measurement performance metrics comprise an overall measurability value that is a product of measurability values associated with each known value of the parameter of interest.

21. The method of claim 19, wherein the one or more measurement performance metrics comprise an overall T-score value that is a weighted sum of T-score values associated with each known value of the parameter of interest, wherein each of the T-score values is a product of the R-score value corresponding to each measurement scenario of the one or more of the subset of the plurality of measurement scenarios and a corresponding indication of a measurement time associated with each measurement scenario.

22. The method of claim 16, wherein the metrology system is any of a spectroscopic ellipsometer, a spectroscopic reflectometer, a single wavelength ellipsometer, and a beam profile reflectometer.

* * * * *